United States Patent [19]

Leveson et al.

[11] Patent Number: 5,176,359

[45] Date of Patent: Jan. 5, 1993

[54] FLUID CONTROL VALVE ARRANGEMENT

[75] Inventors: Richard C. Leveson, Willowdale; Mark D. Bassett, Newmarket, both of Canada

[73] Assignee: Photovac International, Inc., Deer Park, N.Y.

[21] Appl. No.: 703,230

[22] Filed: May 20, 1991

[51] Int. Cl.⁵ .............................................. F16K 7/12
[52] U.S. Cl. .................................. 251/61.1; 137/884
[58] Field of Search ................... 137/884, 606, 607; 251/367, 368, 61.1

[56] References Cited

U.S. PATENT DOCUMENTS

| | | | |
|---|---|---|---|
| 3,094,144 | 6/1963 | Oxley et al. | 251/367 |
| 3,572,368 | 3/1971 | Bullmer | 137/884 |
| 4,703,913 | 11/1987 | Hunkapiller | 137/884 X |
| 4,848,722 | 7/1989 | Webster | 137/884 X |
| 4,869,282 | 9/1989 | Sittler et al. | 251/367 X |
| 4,911,195 | 3/1990 | Farnsworth et al. | 137/606 |

Primary Examiner—Stephen M. Hepperle
Attorney, Agent, or Firm—Skjerven, Morrill, MacPherson, Franklin & Friel

[57] ABSTRACT

A fluid control valve arrangement includes a plurality of clusters or pairs of holes extending from one face to the other of a central block. The valves comprise a plurality of deformable blisters formed in a resilient membrane, the blisters positioned so as to coincide with the hole clusters or pairs when the membrane is pressed against a face of the block. The values are closed when the blisters are deformed to an essentially flat shape, advantageously by introducing a high pressure fluid into a cavity above the blisters. The valves are linked together in a desired configuration by grooves formed in the other face of the block.

17 Claims, 4 Drawing Sheets

FLUID CONTROL VALVE ARRANGEMENT

FIELD OF THE INVENTION

This invention relates to valve systems for controlling the flow of gaseous or liquid fluids and particularly to the precise control valve systems which are required in such fields as gas chromatography.

BACKGROUND OF THE INVENTION

In gas chromatography and other fields, it is necessary to control the flow of one or more fluids by means of an system of control valves. The configuration of the system may be quite complex, and the valves themselves are often required to be very small and precise in operation. To meet this requirement, the internal volume of the valves should be very small.

Moreover, in many applications all surfaces which can come into contact with the controlled fluid must be inert so as to avoid contaminating the fluid. Substances which react with or absorb the controlled fluid can seriously distort the results of a gas chromatography system, for example, since the required sensitivity of those results may be of the order of a few parts per billion, or even less.

It is also desirable that the operation of the valves be as simple as possible and that the valves have a long service life (i.e., numerous openings and closures) without failure.

U.S. Pat. No. 4,353,243 to Martin, issued Oct. 12, 1982, describes an arrangement in which a plurality of diaphragm valves are linked by a peripheral channel formed in the surface of a solid plate. While useful in some applications, this system does not have the flexibility of being adaptable to extremely complex arrays and interconnections between a large number of valves.

SUMMARY OF THE INVENTION

In a fluid control arrangement according to this invention, a plurality of clusters of holes are formed through a block, emerging through opposite faces of the block. Each cluster contains at least two holes. One face of the block is in contact with a resilient membrane (e.g., a thin sheet of steel) which has a plurality of blisters formed in it, the concave side of the blisters facing the block. The blisters are positioned on the membrane so that each blister overlies a cluster of the holes in the block. The hole clusters and blisters comprise the valves of this invention.

In the opposite face of the block, a pattern of grooves or channels is formed on the surface, linking the holes in different clusters. A second resilient membrane is placed in contact with this face of the block. Sealing plates are placed on either side of the block-membrane combination and are pressed firmly against the membranes, so as to prevent fluid from leaking among the holes and grooves. The sealing plate adjacent the membrane with the blisters formed in it has a plurality of holes or recesses formed in it to prevent any contact with the convex surfaces of the blisters. Each of the recesses or holes in this sealing plate is linked by a channel to a source of pressurized fluid. When the pressurized fluid is admitted to the recess or hole overlying a blister, the blister is pressed firmly against the block, thereby sealing off communication between the holes. This closes the valve. When the pressurized fluid is released, the blister springs back to its original shape, thereby opening the valve again. In the case where a reduced pressure is required beneath an "open" valve blister, it may be necessary to reduce the pressure above the blister so as to prevent its collapsing and thereby closing the valve. The grooves or channels on the opposite surface of the block can be formed in any pattern whatsoever, thereby offering the designer complete flexibility in interconnecting the valves. In certain complex applications, it may be desirable to have both channels and valves on the same face of the block, with upper and lower surfaces being used interchangeably.

To provide connections with external equipment, some of the holes do not extend through the entire thickness of the block. Rather, they are linked with channels or galleries which run to the edges of the block where they can be connected with external equipment.

The sealing plates may be formed of a relatively soft material and may have ridges or rings formed around the holes and channels in the block so as to assure that no leakage of fluid between adjacent blisters or channels will occur. Alternatively, the second membrane may be omitted, and the sealing plate may be placed directly against the face of the block in which the interconnecting channels or grooves are formed.

DESCRIPTION OF THE INVENTION

Figure 1A:
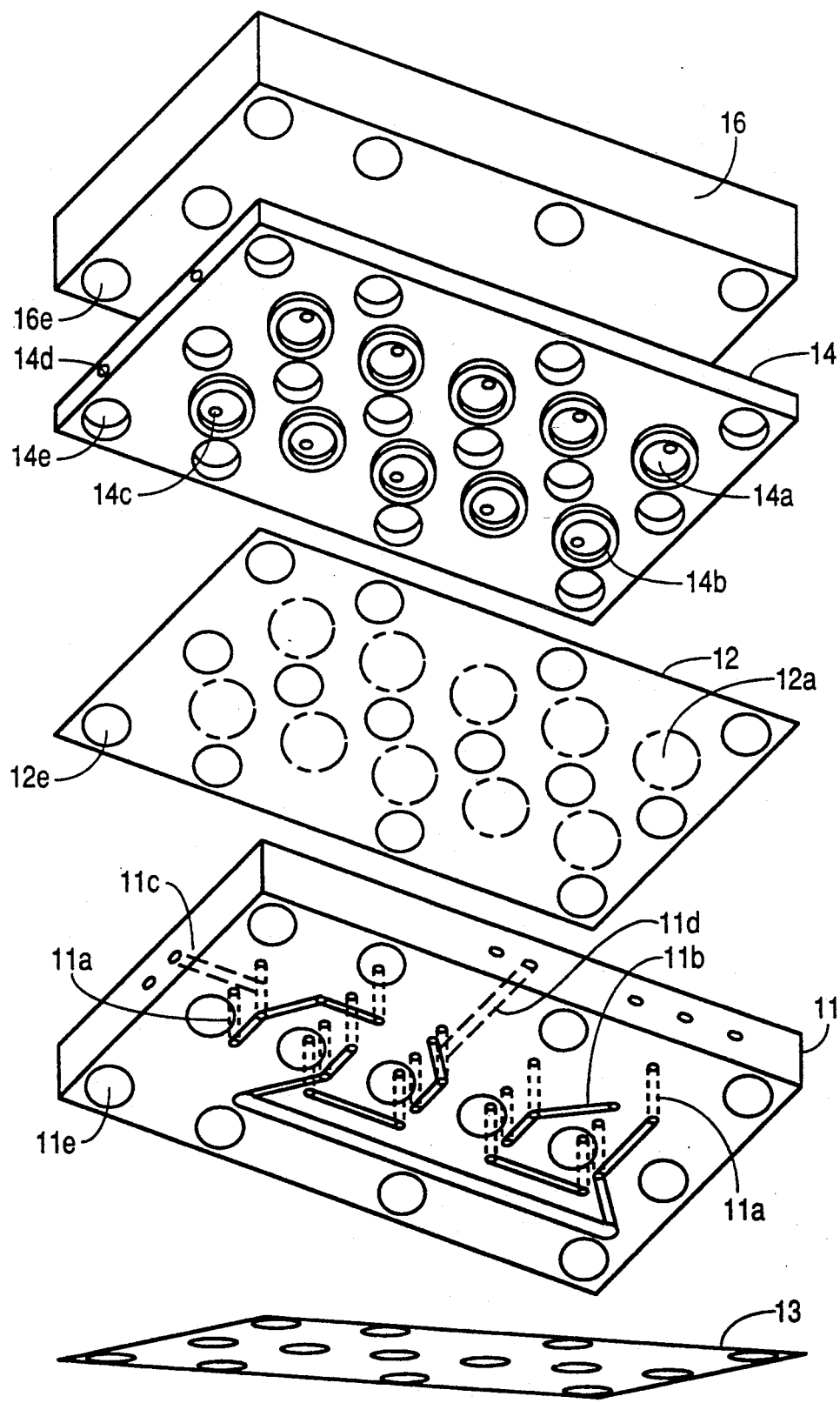
FIG. 1 is an exploded view of a valve arrangement in accordance with this arrangement.
Figure 1B:
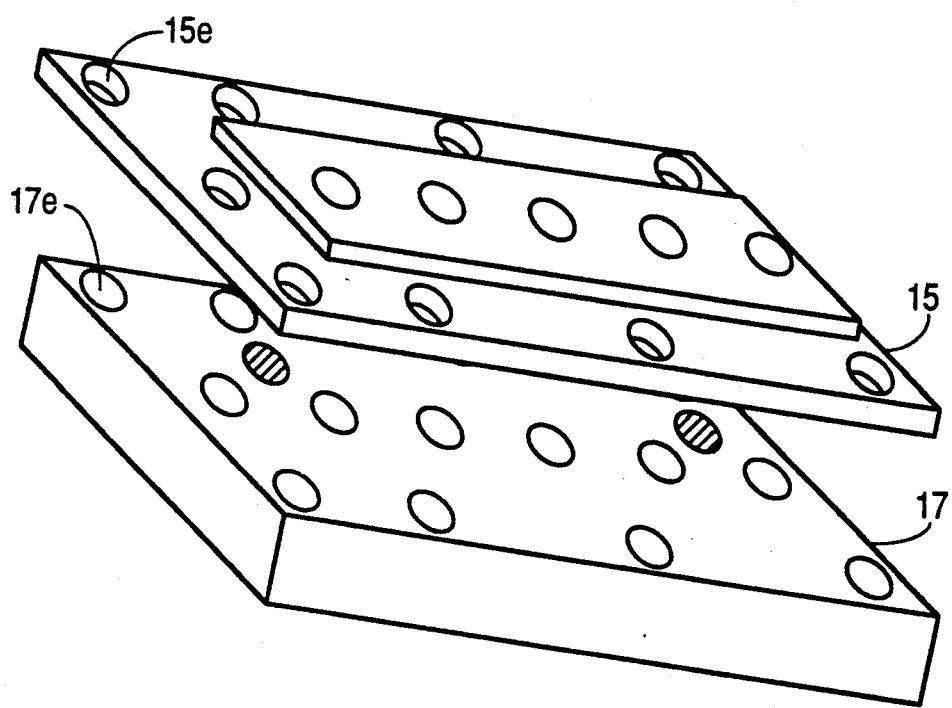

FIG. 1 shows a control valve arrangement 10 which includes a central block 11, membranes 12 and 13, sealing plates 14 and 15, and backing plates 16 and 17. A plurality of holes 11a are formed in clusters (in this embodiment, pairs) in block 11. On the lower surface of block 11, a series of channels 11b link individual holes in each pair with holes in another pair. Channels 11b may also have a second purpose of acting as storage reservoirs for fixed volumes of fluid samples, to be later introduced into the fluid flow for analysis. Horizontal galleries 11c and 11d provide communication between respective holes 11a and an edge of block 11.

Block 11 is preferably formed of a hard material such as a metal, ceramic, hard polymer or polymer composite. The upper and lower faces of block 11 are substantially parallel and each is highly polished to enhance sealing with membranes 12 and 13 or with membrane 12 and sealing plate 15, when membrane 13 is omitted.

Membrane 12 is a thin sheet of metal or of a resilient polymer or elastomer which has a plurality of blisters 12a formed or impressed into it. Each of blisters 12a has a concave surface facing block 11 and a convex surface facing sealing plate 14. Blisters 12a are positioned so that each of them registers with a single pair of holes 11a. Membrane 13, which is in the form of a flat sheet, is placed against the lower side of block 11. Membranes 12 and 13 may be manufactured from a metal, polymer, polymer composite or elastomer. Membrane 12 may be made of the same material as membrane 13, but need not be. Membranes 12 and 13 must be thin and smooth enough to form a leakproof seal with the polished faces of block 11 and, in the case of membrane 12, must be resilient enough to allow blisters 12a to be deformed repeatedly without affecting their ability to return to their normal shape. Moreover, where the controlled fluid must come into contact with only inert surfaces, block 11 and membranes 12 and 13 should be made of a material such as stainless steel or, in particularly demanding applications, stainless steel coated with a highly inert material such as gold or silver.

Membranes 12 and 13 are pressed against block 11 by sealing plates 14 and 15, respectively. As shown in FIG. 1, sealing plate 14 has a series of recesses 14a formed in it. Each of recesses 14a coincides with the position of one of blisters 12a, and forms a cavity which allows the blister to assume its normal shape when sealing plate 14 is pressed against block 11. Surrounding each of recesses 14a on the surface of plate 14 is a ring 14b. When plate 14 is pressed firmly against block 11, rings 14b press down hard on membrane 12 and form a particularly tight seal between membrane 12 and block 11 around each pair of holes 11a.

Similarly, sealing plate 15 has ridges formed in its upper surface which surround each of grooves 11b when it is pressed against block 11 (these ridges are not shown in FIG. 1.) The ridges, functioning similarly to rings around each of grooves 11b.

Each of recesses 14a contains an aperture 14c which communicates through a channel with an aperture 14d on the edge of plate 14, so as to allow the entry of a driver fluid into recesses 14a, as described below. Recesses 14a, rings 14b and apertures 14c and d are best seen in the cross-sectional view of FIG. 2.

Sealing plates 14 and 15 are preferably made of a soft material such as a polymer, elastomer, graphite fiber or a soft metal such as copper.

As an alternative to recesses 14b, space for blisters 12a may be provided by holes formed through the entire thickness of plate 14.

Backing plates 16 and 17 are formed of a relatively hard material and provide support as sealing plates 14 and 15 and membranes 12 and 13 are pressed tightly against block 11. The entire structure of FIG. 1 is clamped together by bolts (not shown) which extend through holes which line up when each member of the structure is properly positioned. These holes are not individually numbered in FIG. 1 but are exemplified by holes 11e–17e. It will be apparent that care must be taken in designing the positions of holes 11a and channels 11b to avoid any conflict with the mounting holes in block 11.

Figure 2:
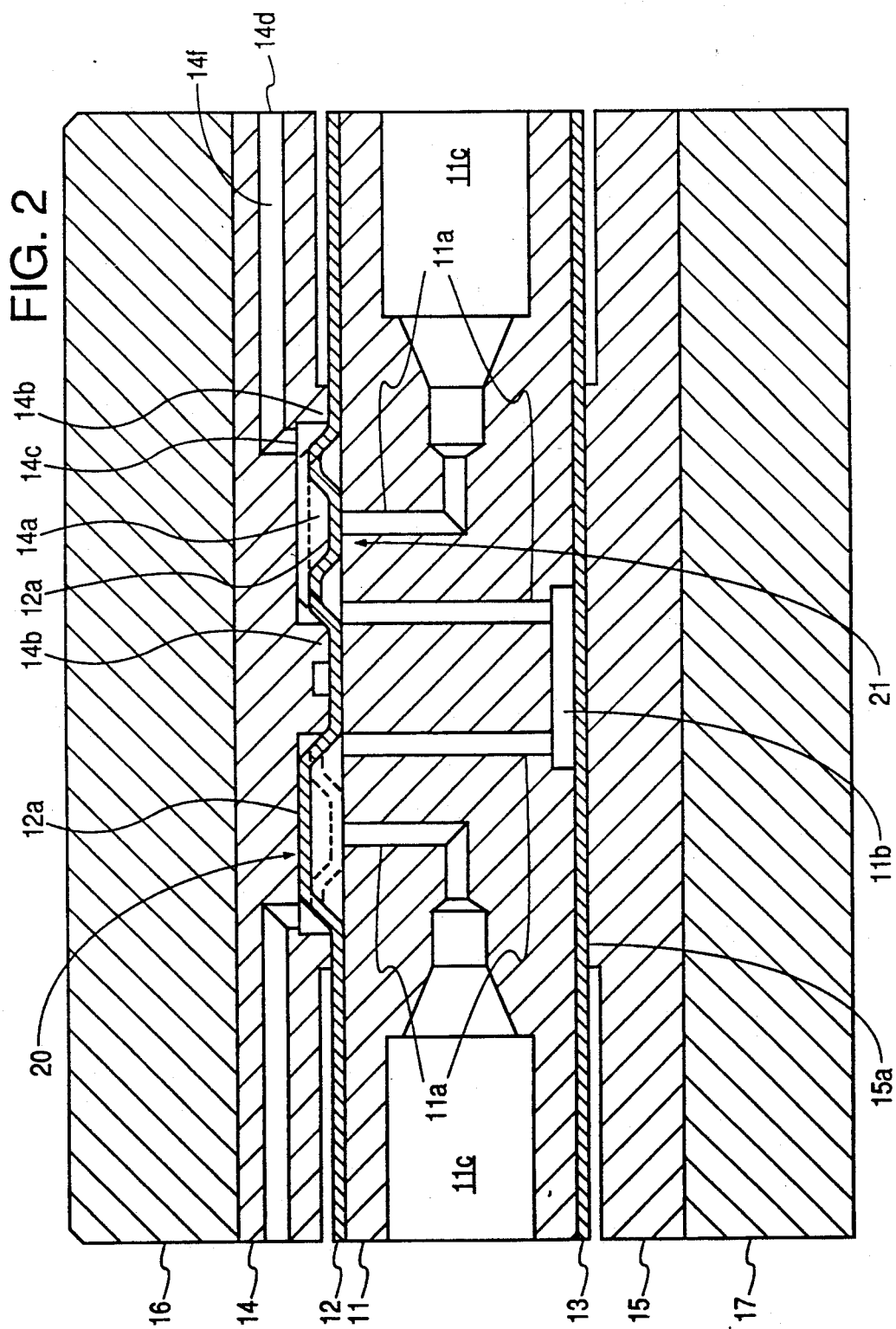
FIG. 2 is an illustrative cross-sectional view of two valves in accordance with this invention.

FIG. 2 is an illustrative cross-sectional view showing the construction of two valves 20 and 21 in accordance with the invention. Elements identified in FIG. 1 have been designated with the same numbers in FIG. 2 and, in addition, FIG. 2 shows a cross-sectional view of a ridge 15a in sealing plate 15 which surrounds and provides a leakproof seal for groove 11b. Thus, each of valves 20 and 21 includes the following elements a blister 12a in membrane 12, two holes 11a in block 11, and a recess 14a in sealing plate 14 surrounded by ring 14b. The vertical dimensions of blisters 12a and recesses 14a are expanded somewhat for reasons of clarity. A height of blisters 12a in the range of 0.02 mm to 0.2 mm. has been found to give satisfactory results. Each of recesses 14a has an aperture 14c which leads through a channel 14f to an external aperture 14d. Aperture 14d is connected to a source of pressurized drive fluid (not shown). Two of holes 14a extend all the way through block 11 and are linked on the bottom surface of block 11 by a channel 11b. The remaining holes 11a extend approximately half-way through block 11 and are joined with horizontal galleries 11c leading to the outside edge of block 11.

Thus, when the valves 20 and 21 are open (as represented by valve 20) fluid is able to flow, for example, from gallery 11c on the left, through valve 20, through the holes 11a linked with channel 11b, and through valve 21 into gallery 11c on the right.

Valve 21 is shown in a closed position. This is accomplished by introducing a pressurized fluid through channel 14f into recess 14a. As illustrated in FIG. 2, this forces the flexible blister 12a downward against the aperture of hole 11a which is centrally located in valve 21. Blister 12a is pressed firmly against hole 11a, thereby closing off fluid flow through valve 21. When the pressurized fluid is released from recess 14a, blister 12a springs back to its normal position, as represented by valve 20, thereby restoring fluid flow between the holes 11a and opening the valve.

It should be understood that FIG. 2 shows only a representative structure containing two valves 20 and 21. This structure can be expanded to encompass numerous valves which are linked by grooves 11b or connected to horizontal galleries 11c in any pattern or configuration required by the particular application. The valves of the structure are extremely precise and responsive and can be manufactured with resilient membranes made of such materials as stainless steel which are capable of sustaining numerous openings and closing without fatigue or failure. Moreover, the valves may be easily designed so that the controlled fluid comes into contact with only inert surfaces and therefore suffers no contamination from passing through the valve structure.

Figure 3:
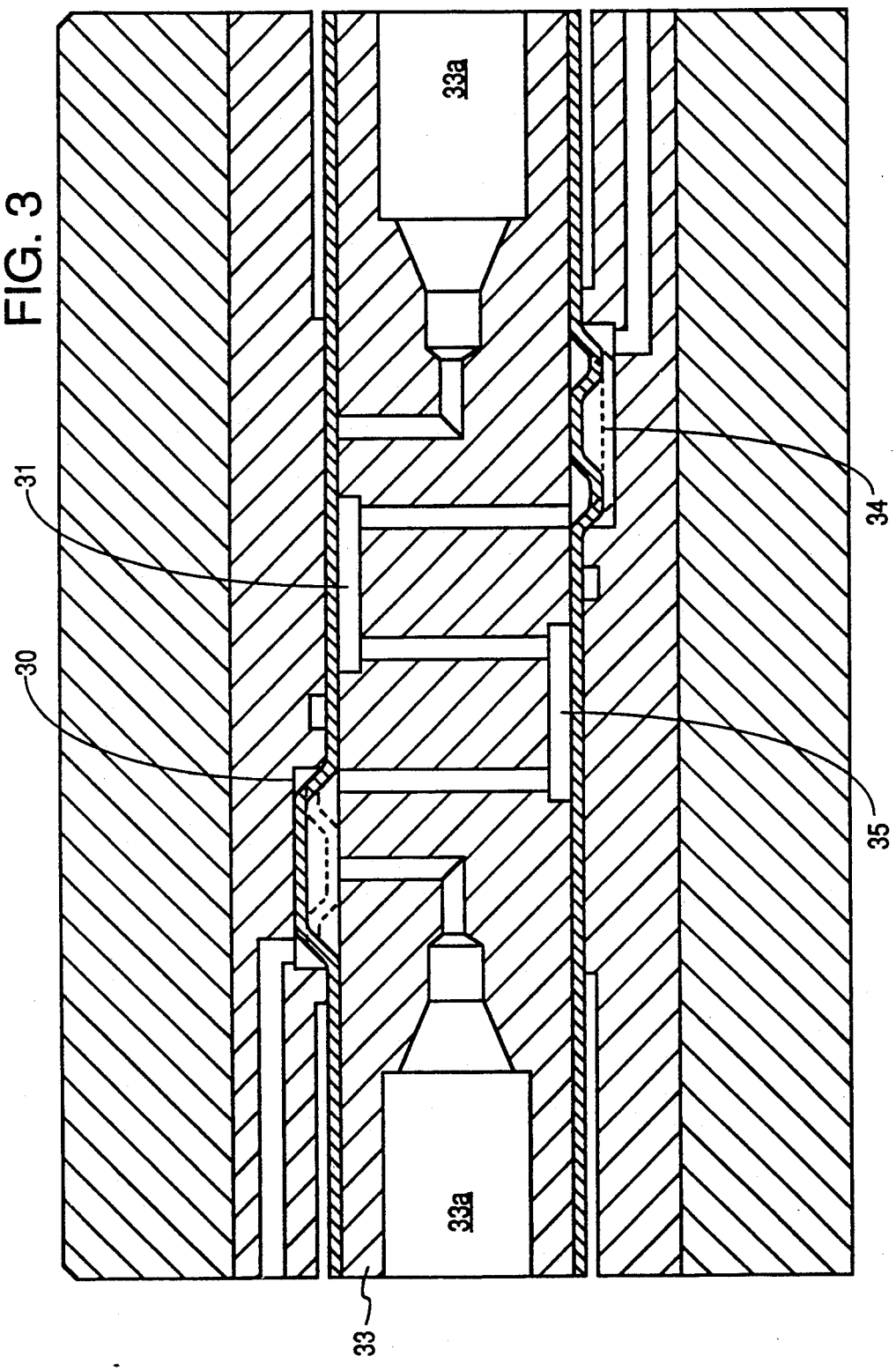
FIG. 3 is an illustrative cross-sectional view of another embodiment in accordance with the invention.

Moreover, where the complexity of the configuration demands, a control valve arrangement of this invention may include blister valves and connecting grooves on both faces of the central block. Such an arrangement is illustrated in FIG. 3, which shows a valve 30 and a groove 31 in the upper face of a block 33, and a valve 34 and a groove 35 in the lower face of block 33. Valves 30 and 34 and grooves 31 and 35 are connected in series between galleries 33a in block 33. Valves 30 and 34 are similar in construction and operate in the same manner as valves 20 and 21 in FIG. 2.

The embodiments described above are illustrative and not limiting of the invention. Many additional and alternative embodiments will be apparent to those skilled in the art, all of which are in the broad scope of this invention.

We claim:
1. A fluid control valve arrangement comprising:
a block having a plurality of clusters of holes, said holes extending from a first face of said block to a second face of said block and certain of said holes being linked by one or more grooves formed in the second face of said block;
a first membrane pressed against the first face of said block, said membrane having a plurality of blisters, each of said blisters being permanently formed in said membrane, with a convex side and a concave side, and being positioned with the concave side thereof facing one of said hole clusters;
sealing means positioned adjacent the second face of said block, said sealing means providing a seal around each of said one or more grooves;
wherein individual ones of said blisters are deformable by the creation of a pressure differential between the convex and concave sides thereof so as to prevent the flow of fluid through the hole clusters associated with said deformed blisters, the pressure on the convex side of the blister being greater than the pressure on the concave side of the blister when the blister is deformed.

2. The fluid control valve arrangement of claim 1 comprising means for allowing a controlled fluid to flow into at least one of said holes and means for allowing said controlled fluid to flow out of at least another one of said holes.

3. The fluid control valve arrangement of claim 2 comprising a first sealing plate for pressing said first membrane against the first face of said block, said first sealing plate including recesses which coincide with the respective locations of said blisters in said first membrane.

4. The fluid control valve arrangement of claim 3 comprising means for selectively deforming individual ones of said blisters.

5. The fluid control valve arrangement of claim 4 wherein said deforming means comprises means for selectively introducing a pressurized fluid into individual ones of said recesses.

6. The fluid control valve arrangement of claim 3 wherein said sealing means comprises a second sealing plate pressed against the second face of said block.

7. The fluid control valve of claim 3 wherein said sealing means comprises a second membrane and a second sealing plate, said second sealing plate being positioned so as to press said second membrane against the second face of said block.

8. The fluid control valve arrangement of claim 6 wherein said second sealing plate contains ridges which surround individual ones of said grooves.

9. The fluid control valve arrangement of claim 3 wherein said first sealing plate contains a plurality of rings, each of said rings surrounding one of said hole clusters.

10. The fluid control valve arrangement of claim 6 wherein said block, said first membrane and said second sealing plate are made of an inert material.

11. The fluid control valve arrangement of claim 7 wherein said block and said first membrane and second membrane are made of an inert material.

12. The fluid control valve arrangement of claim 11 wherein said inert material is selected from the group consisting of stainless steel, a nickel steel alloy, a chromium steel alloy, a nickel/chromium steel alloy, a material coated with gold and a material coated with a metal of the platinum group.

13. A fluid control valve arrangement comprising:
a block having a plurality of clusters of holes, said holes extending from a first face of said block to a second face of said block and certain of said holes being linked by grooves, at least one of said grooves being formed in the first face of said block and at least one of said grooves being formed in the second face of said block
a first membrane pressed against the first face of said block, said first membrane having a plurality of blisters, each of said blisters being permanently formed in said membrane, with a convex side and a concave side, and being positioned with the concave side thereof facing one of said hole clusters;
a second membrane pressed against the second face of said block, said second membrane having a plurality of blisters, each of said blisters being permanently formed in said membrane, with a convex side and a concave side, and being positioned with the concave side thereof facing another one of said hole clusters;
sealing means positioned adjacent the first and second faces said block, said sealing means providing a seal around each of said grooves;
wherein individual ones of said blisters are deformable by the creation of a pressure differential between the convex and concave sides thereof so as to prevent the flow of fluid through the hole clusters associated with said deformed blisters, the pressure on the convex side of the blister being greater than the pressure on the concave side of the blister when the blister is deformed.

14. The fluid control valve arrangement of claim 13 wherein said first and second membranes comprise said sealing means.

15. The fluid control valve arrangement of claim 14 wherein said block and said first membrane and said second membrane are made of an inert material.

16. The fluid control valve arrangement of claim 15 wherein said inert material is selected from the group consisting of stainless steel, a nickel steel alloy, a chromium steel alloy, a nickel/chromium steel alloy, a material coated with gold and a material coated with a metal of the platinum group.

17. A fluid control valve arrangement comprising:
a block having a plurality of clusters of holes, said holes extending from a first face of said block to a second face of said block and certain of said holes being linked by one or more grooves formed in the second face of said block;
a first membrane pressed against the first face of said block, said membrane having a plurality of blisters formed in it, said blisters being positioned so as to coincide with the locations of said hole clusters;
a first sealing plate for pressing said first membrane against the first face of said block, said first sealing plate including recesses which coincide with the respective locations of said blisters in said first membrane;
sealing means positioned adjacent the second face of said block, said sealing means comprising a second sealing plate pressed against the second face of said block, said second sealing plate containing ridges which surround individual ones of said grooves so as to provide a seal around each of said grooves; and
means for allowing a controlled fluid to flow into at least one of said holes and means for allowing said controlled fluid to flow out of at least another one of said holes;
wherein individual ones of said blisters are deformable so as top prevent the flow of fluid through the hole clusters associated with said deformed blisters.

* * * * *